United States Patent
Candidus et al.

(10) Patent No.: US 9,426,559 B2
(45) Date of Patent: Aug. 23, 2016

(54) HEARING PROTECTION DEVICE

(71) Applicants: Yvonne Candidus, Fürth (DE);
Hubertus Fischer, Bamberg (DE)

(72) Inventors: Yvonne Candidus, Fürth (DE);
Hubertus Fischer, Bamberg (DE)

(73) Assignee: Siemens Aktiengesellschaft, München (DE)

(*) Notice: Subject to any disclaimer, the term of this patent is extended or adjusted under 35 U.S.C. 154(b) by 0 days.

(21) Appl. No.: 14/695,875

(22) Filed: Apr. 24, 2015

(65) Prior Publication Data

US 2015/0312670 A1 Oct. 29, 2015

(30) Foreign Application Priority Data

Apr. 24, 2014 (DE) .................. 10 2014 207 705

(51) Int. Cl.
| | |
|---|---|
| *H04R 25/00* | (2006.01) |
| *H04R 1/10* | (2006.01) |
| *A61F 11/14* | (2006.01) |
| *G01R 33/28* | (2006.01) |
| *A61B 5/055* | (2006.01) |

(52) U.S. Cl.
CPC .............. *H04R 1/1083* (2013.01); *A61F 11/14* (2013.01); *G01R 33/283* (2013.01); *G01R 33/288* (2013.01); *A61B 5/055* (2013.01); *A61F 2250/0003* (2013.01); *H04R 1/1008* (2013.01)

(58) Field of Classification Search
CPC ............................ H04R 25/00; H04R 1/1008
USPC ................................................. 181/128, 129
See application file for complete search history.

(56) References Cited

U.S. PATENT DOCUMENTS

| | | | | |
|---|---|---|---|---|
| 3,602,329 | A * | 8/1971 | Bauer et al. .................. | 181/129 |
| 4,572,323 | A * | 2/1986 | Randall ........................ | 181/129 |
| 5,519,783 | A * | 5/1996 | Kumar .......................... | 381/370 |
| 5,551,090 | A * | 9/1996 | Thompson ..................... | 2/209 |
| 2003/0034198 | A1* | 2/2003 | Cushman et al. ............. | 181/129 |
| 2013/0087404 | A1* | 4/2013 | Peskar et al. ................. | 181/129 |
| 2013/0153328 | A1* | 6/2013 | Carolan et al. ............... | 181/129 |
| 2013/0319788 | A1* | 12/2013 | Franzen ........................ | 181/129 |
| 2014/0364722 | A1* | 12/2014 | Dumoulin .................... | 600/415 |
| 2015/0041243 | A1* | 2/2015 | Ratliff .......................... | 181/129 |

FOREIGN PATENT DOCUMENTS

WO WO2007138309 A2 12/2007

OTHER PUBLICATIONS

Wikipedia; "Isomatte," Wikipedia, freie Enzyklopädie, URL: http://de.wikipedia.org/w/index.php?title=Isomatte&oldid=90885025, pp. 1-2, Jul. 5, 2011.
German Office Action for German Application No. 10 2014 207 705.2, mailed Jan. 22, 2015, with English Translation.

* cited by examiner

*Primary Examiner* — Forrest M Phillips
(74) *Attorney, Agent, or Firm* — Lempia Summerfield Katz LLC

(57) ABSTRACT

A hearing protection device for use in magnetic resonance devices is provided. The hearing protection device has a first hearing protection unit for disposal on a first ear of a patient and a second hearing protection unit for disposal on a second ear of a patient. The first hearing protection unit and/or the second hearing protection unit has a fluid cushion unit.

16 Claims, 1 Drawing Sheet

HEARING PROTECTION DEVICE

This application claims the benefit of DE 10 2014 207 705.2, filed on Apr. 24, 2014, which is hereby incorporated by reference in its entirety.

BACKGROUND

The present embodiments relate to a hearing protection device for use in magnetic resonance devices.

With magnetic resonance examinations, for example, a noise-protection headset is used for noise reduction (e.g., for shielding the patient from sound waves) and for communication between a patient and operating personnel in charge of the magnetic resonance examination. For noise reduction, the noise reduction headset is provided with massive plastic elements on the ear pieces. This leads to the noise reduction headsets being heavy and also needing a large amount of space.

If such noise reduction headsets are used together with a head coil unit, this may lead to the noise reduction headset slipping from an intended position on the patient's head because of the small amount of space available within the head coil unit. In addition, as a result of this direct contact between the head coil unit and the massive noise protection headsets, an undesired sound transmission may occur.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a lightweight hearing protection device that may be positioned on the patient easily and securely is provided.

A hearing protection device for use in magnetic resonance facilities is provided. The hearing protection device includes a first hearing protection unit for disposal on a first ear of a patient and a second hearing protection unit for disposal on a second ear of a patient.

The first hearing protection unit and/or the second hearing protection unit have a fluid cushion unit. A fluid cushion unit may be understood as a unit that has a fluid cushion. In one embodiment, the at least one fluid cushion has an impermeable shell with respect to an exchange of a fluid (e.g., a gaseous fluid) that surrounds an area for receiving a fluid (e.g., a gaseous fluid). The area for receiving the fluid may be configured to be exclusively filled or able to be filled by the fluid, such as air, for example, or may also contain filler materials such as a foam material, for example. During a filling, the fluid may be received at least partly into spaces and/or bubbles between individual filler material elements. In one embodiment, a filler space enclosed by the shell to accept the fluid of the fluid cushion unit is able to be embodied variably with respect to volume and/or an extent. The hearing protection device may include a noise reduction headset, using which protects a patient from noise (e.g., during a magnetic resonance examination). Also, communication between the patient and operating personnel in charge of the magnetic resonance examination may be provided.

This embodiment enables a hearing protection device that may be used flexibly. The hearing protection device may be positioned on the patient in a space-saving manner such as, for a head examination, together with a head coil unit in which the space available for the hearing protection device is restricted. Because of the fluid cushion unit, a shape and/or contour of the hearing protection device may be embodied flexibly and/or variably. An optimum and/or an ideal hearing protection position of the hearing protection device may be maintained on an ear of the patient. This enables advantageous shielding from noise (e.g., during a magnetic resonance examination) to be achieved for a patient. In one embodiment, the fluid cushion unit may be supplied with a fluid after the fluid cushion unit has been positioned on the patient, so that through this, a position of the hearing protection device (e.g., the first hearing protection unit on the first ear of the patient and the second hearing protection unit on the second ear of the patient) may be achieved for an advantageous noise shielding for the patient.

In one embodiment, the first hearing protection unit has a first ear pad with a first ear accommodating area and a second ear pad with the second ear accommodating area. The fluid cushion is disposed on a side of the first ear pad facing away from the first ear accommodating area and/or on a side of the second ear pad facing away from the second ear accommodating area. This further allows an advantageous ability to position the hearing protection device on the patient to be achieved and in addition enables an especially efficient noise reduction for the patient to be achieved. In addition, massive components of the hearing protection device that, for example, were previously present for noise screening and/or noise absorption may advantageously be replaced by the fluid cushion unit, so that an especially lightweight hearing protection device may be provided. Using this embodiment of the hearing protection device, the first ear pad of the first hearing protection unit and/or the second ear pad of the second hearing protection unit, because of the fluid cushion unit, may be advantageously shielded from noise (e.g., from sound waves).

The fluid cushion unit has at least one fluid cushion able to be filled with a filler substance. In this way, a size and/or shape of the fluid cushion unit (e.g., of the at least one fluid cushion) is able to be adapted easily to an examination position of the patient. Feeding a filler formed from a fluid (e.g., a gaseous filler) into the at least one fluid cushion (e.g., inflating the fluid cushion with air) may take place only once the patient has been positioned together with the hearing device within a head coil unit, so that the hearing protection device takes up little space during the positioning. Thus, the hearing protection device, in a state positioned on the patient, may be prevented from slipping. In addition, by feeding the filler (e.g., a gaseous filler) into the at least one fluid cushion, the patient (e.g., the head of the patient), for example, may be supported within a head coil free from play and/or free from movement, so that an undesired movement of the head by the patient is prevented.

In an embodiment, the fluid cushion unit has at least one fluid cushion that includes a foam material. The foam material, in a first operating state, is compressed and in a second operating state, because of the spring force of the foam material, expands and accepts a filler. In one embodiment, the filler includes a gaseous filler. Through this embodiment, for example, an automatic expansion and taking up of the filler (e.g., the gaseous filler) may take place. Thus, a simple preparation of the patient for the impending magnetic resonance examination may be achieved. In one embodiment, the take-up and removal of the filler (e.g., the gaseous filler) may be regulated by a valve of the fluid cushion unit. In the first operating state, the foam material, because of the force acting from the outside on the fluid cushion, is compressed so that the filler escapes from the fluid cushion. In the second operating state, this force acting from outside is no longer present, such as, for example, by opening a valve of the fluid cushion, so that the filler (e.g., air) may penetrate into the cushion and may accumulate in spaces and/or bubbles between individual filler material elements.

The filler may include air. A low-cost filler may thus be provided for the fluid cushion unit. In addition, availability of the filler may be guaranteed at any time through this. Further fillers (e.g., gaseous fillers and/or fluid fillers) may be provided.

In one embodiment, the hearing protection device includes a pump unit for feeding a fluid into the fluid cushion unit of the first hearing protection unit and/or the second hearing protection unit. A simple and rapid feeding of the fluid into the at least one fluid cushion of the fluid cushion unit may be achieved, such as inflating and/or pumping up a fluid cushion with air by the pump unit, for example. In one embodiment, the pump unit is disposed removably on the fluid cushion unit so that the pump unit is only connected to the fluid cushion unit during the filling process, and the pump unit may be removed (e.g., during magnetic resonance examinations). Any influencing of the magnetic resonance examination by the pump unit may thus be prevented.

In one embodiment, the pump unit includes a mechanical pump unit, such as a mechanical hand pump unit, for example. In addition, further embodiments of the pump unit appearing sensible to the person skilled in the art may be provided. For example, an electric pump unit may also be used if the electric pump unit is used exclusively outside the magnetic resonance device.

The fluid cushion unit includes at least one fluid cushion with at least one opening for supplying a fluid and/or for draining off a fluid. This enables the fluid cushion unit (e.g., the at least one fluid cushion of the fluid cushion unit) to be configured variably with respect to a volume and/or shape.

If the fluid cushion unit has at least a fluid cushion with at least one valve unit, an advantageous control of a fill level of a fluid (e.g., of air) within the at least one fluid cushion may be achieved.

In one embodiment, a magnetic resonance device with a hearing protection device is provided. This embodiment allows for a hearing protection device for a magnetic resonance examination on a patient that may be used flexibly. In one embodiment, the hearing protection device may be positioned on the patient in a space-saving manner, such as for a head examination together with a head coil unit, for example, in which the space available for the hearing protection device is restricted. Further, as a result of the fluid cushion unit of the hearing protection device, a shape and/or contour of the hearing protection device may be configured flexibly and/or variably. An optimum and/or an ideal hearing protection position of the hearing protection device may be maintained on an ear of the patient.

The advantages of the magnetic resonance device of one or more of the present embodiments essentially correspond to the advantages of the hearing protection device of one or more of the present embodiments, which have been explained in detail above. Features, advantages or alternate forms of embodiments mentioned here may likewise be transferred to the other subject matter and vice versa.

DETAILED DESCRIPTION

Figure 1:
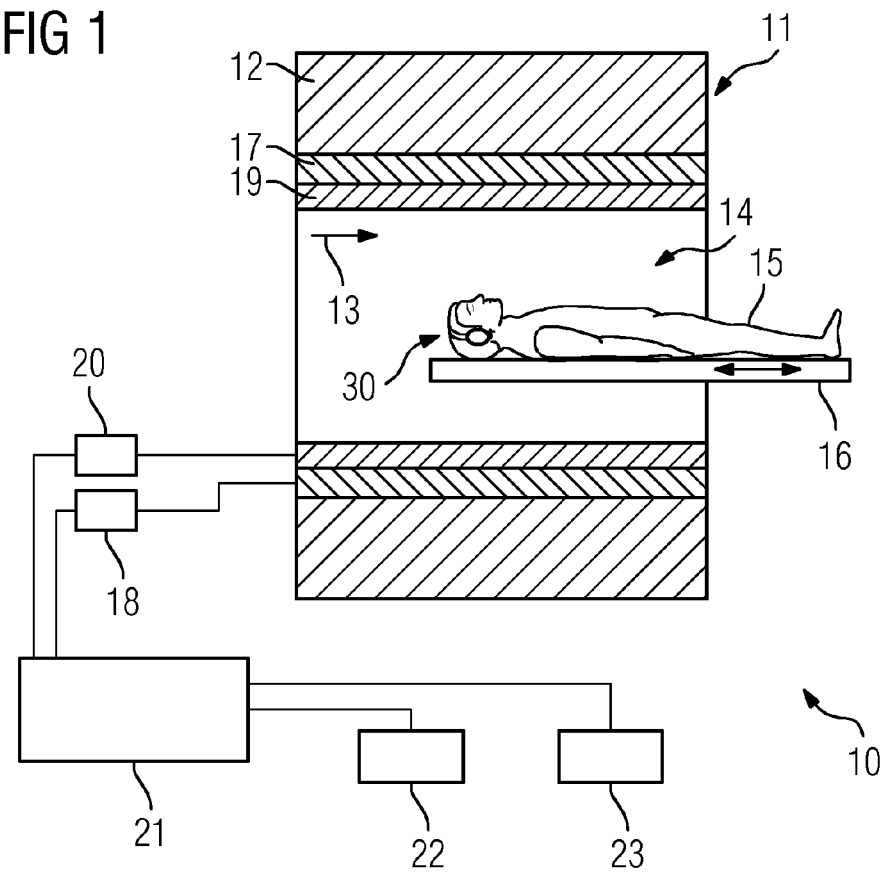
FIG. 1 shows one embodiment of a magnetic resonance device in a schematic diagram.

FIG. 1 shows a schematic diagram of one embodiment of a magnetic resonance device 10 (e.g., a magnetic resonance device). The magnetic resonance device 10 includes a magnet unit 11 with a superconducting main magnet 12 for creating a strong and, for example, constant main magnetic field 13. In addition, the magnetic resonance device 10 has a patient receiving area 14 for receiving a patient. In the present exemplary embodiment, the patient receiving area 14 is embodied in a cylindrical shape and is surrounded in a circumferential direction by the magnet unit 11 in the shape of a cylinder. An embodiment of the patient receiving area 14 differing therefrom may, however, be provided. The patient 15 may be pushed into the patient receiving area 14 by a patient support device 16 of the magnetic resonance device 10.

The magnet unit 11 also includes a gradient coil unit 17 for creating magnetic field gradients that are used for local encoding during imaging. The gradient coil unit 17 is controlled by a gradient control unit 18 of the magnetic resonance device 10. The magnet unit 11 further includes a radio-frequency antenna unit 19 for exciting a polarization that occurs in the main magnetic field 13 created by the main magnet 12. The radio-frequency antenna unit 19 is controlled by a radio-frequency antenna control unit 20 of the magnetic resonance device 10. The radio-frequency antenna unit 19 radiates radio-frequency magnetic resonance sequences into an examination area that is essentially formed by a patient receiving area 14 of the magnetic resonance device 10.

To control the main magnet 12, the gradient control unit 18, and the radio-frequency antenna control unit 20, the magnetic resonance device 10 includes a control unit 21 formed by a processing unit. The control unit 21 centrally controls the magnetic resonance device 10, such as, for example, carrying out a predetermined imaging gradient echo sequence. In addition, the control unit 21 includes an evaluation unit not shown in any greater detail for evaluating image data. Control information, such as imaging parameters, for example, as well as reconstructed magnetic resonance images, may be displayed on a display unit 22 (e.g., on at least one monitor) of the magnetic resonance device 10 for an operator. In addition, the magnetic resonance device 10 includes an input unit 23, by which information and/or parameters may be entered by an operator during a measurement process.

To protect the patient 15 from noise during a magnetic resonance examination, a hearing protection device 30 that is enclosed by the magnetic resonance device 10 is provided. In the present exemplary embodiment, the hearing protection device 30 includes a noise reduction headset, by which both communication between operating personnel in charge of the magnetic resonance examination and the patient 15 as well as an effective protection against noise emanating from the magnetic resonance device 10 (e.g., the magnet unit 11) may be provided. In the present exemplary embodiment, the hearing protection device 10 (e.g., the noise reduction headset) includes on-ear ear pads and/or in-ear ear pads.

Figure 2:
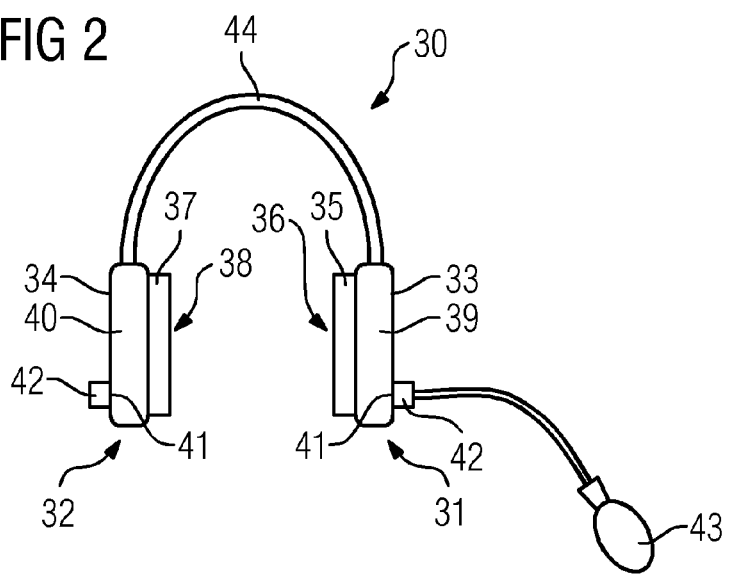
FIG. 2 shows one embodiment of a fluid cushion unit of the magnetic resonance device in a schematic diagram.

FIG. 2 shows the hearing protection device 30 from FIG. 1 in greater detail. The hearing protection device 30 has a first hearing protection unit 31 for disposal on a first ear of a patient 15 and a second hearing protection unit 32 for disposal on a second ear of the patient 15. The first hearing protection unit 31 includes a first fluid cushion unit 33, and the second hearing protection unit 32 includes a second fluid cushion unit 34. The first hearing protection unit 31 includes a first ear pad 35 with a first ear accommodating area 36. The first fluid cushion unit 33 is disposed on a side of the first ear pad 35 of the first hearing protection unit 31 facing away from the first ear accommodating area 36. The second hearing protection unit 32 has a second ear pad 37 with a second ear accommodating area 38. The second fluid cushion unit 34 is disposed on a side of the ear pad 37 of the second hearing protection unit 32 facing away from the second ear accommodating area 38. The first hearing protection unit 31 and the second hearing protection unit 32 are connected to each other by a band 44 of the hearing protection device.

In an embodiment of the hearing protection device 30 differing therefrom, the connection by the band 44 between the first hearing protection unit 31 and the second hearing protection unit 32 may be omitted.

The first fluid cushion unit 33 and the second fluid cushion unit 34 each have a fluid cushion 39, 40 that in the present exemplary embodiment is able to be filled with the gaseous filler. The gaseous filler may be formed by all gaseous fillers appearing sensible to the person skilled in the art. In one embodiment, the gaseous filler includes air, so that an advantageous availability of the filler may be achieved. As an alternative or in addition, the filler may include a fluid filler and/or further fluids appearing sensible to the person skilled in the art.

The fluid cushion 39 of the first fluid cushion unit 33 and the fluid cushion 40 of the second fluid cushion unit 34 each have a shell that surrounds a filling space for receiving the gaseous filler. The shell is embodied tightly sealed in each case with respect to an exchange of the gaseous filler. In addition, the shell of the fluid cushion 39 of the first fluid cushion unit 33 and the shell of the fluid cushion 40 of the second fluid cushion unit 34 include a flexible shell that is, for example, variable and/or flexible with respect to volume and/or shape. The shell of the fluid cushion 39 of the first fluid cushion unit 33 and the shell of the fluid cushion 40 of the second fluid cushion unit 34 may be formed from a magnetic resonance-compatible material, such as by an artificial leather and/or Polyvinylchloride (PVC) film and/or Polyurethane (PU)-coated and/or further materials appearing sensible to the person skilled in the art.

The fluid cushion 39 of the first fluid cushion unit 33 and the fluid cushion 40 of the second fluid cushion unit 34 each have an opening 41. The fluid (e.g., air) may be supplied by the openings 41, and the fluid formed by the air may be removed from the fluid cushion 39, 40. Disposed within the opening 41 of the fluid cushions 39 of the first fluid cushion unit 33 is a valve unit 42 of the first fluid cushion unit 33. Disposed within the opening 41 of the fluid cushion 40 of the second fluid cushion unit 34 is a valve unit 42 of the second fluid cushion unit 34.

The hearing protection device 30 also includes a pump unit 43 that in the present exemplary embodiment is formed by a mechanical hand pump unit. Using the mechanical hand pump unit, air may be pumped via the valve units 42 and the openings 41 into the individual fluid cushions 39, 40. The pump unit 43 is embodied removably on the fluid cushions 39, 40, so that a single pump unit 43 may be used for both fluid cushions 39, 40 of the first fluid cushion unit 33 and the second fluid cushion unit 34.

In one embodiment, the fluid cushion 39 of the first fluid cushion unit 33 and the fluid cushion 40 of the second fluid cushion unit 34 may be filled at the same time by a single pump unit 43. The pump unit 43 may be connected by a Y-adapter and/or a Y-piece to the valve units 42 of the fluid cushion 39 of the first fluid cushion unit 33 and of the fluid cushion 40 of the second fluid cushion unit 34.

In one embodiment, the individual fluid cushions 39, 40 of the first fluid cushion unit 33 and the second fluid cushion unit 34 are pumped up after the patient 15 has been positioned on the patient support device 16 and, if necessary, after the head of the patient 15 has been positioned, together with the hearing protection device 30, within a head coil unit not shown in any greater detail. The individual fluid cushions 39, 40 may also be pumped up before an introduction of the patient 15 into the patient receiving area 14. In addition, the fluid cushions 39, 40 filled with air enable the patient 15 (e.g., the head of the patient 15) to be supported without play within the head coil unit, so that an undesired movement may be prevented.

The filler space of the fluid cushion 39 of the first fluid cushion unit 33 surrounded by the shell and/or the filler space of the fluid cushion 40 of the second fluid cushion unit 34 surrounded by the shell may be formed exclusively by the gaseous filler formed from air. As an alternative, the filler space of the fluid cushion 39 of the first fluid cushion unit 33 surrounded by the shell and/or the filler space of the fluid cushion 40 of the second fluid cushion unit 34 surrounded by the shell may also include a foam material. This foam material is compressed in a first operating state (e.g., as a result of an external pressure on the fluid cushion 39 of the first fluid cushion unit 33 and/or on the fluid cushion 40 of the second fluid cushion unit 34) so that the fluid cushions 39 of the first fluid cushion unit 33 and/or the fluid cushion 40 of the second fluid cushion unit 34 occupies a minimal volume.

In a second operating state, the pressure acting on the fluid cushion 39 of the first fluid cushion unit 33 and/or on the fluid cushion 40 of the second fluid cushion unit 34 falls away (e.g., as a result of opening the valve unit 42 of the first fluid cushion unit 33 and/or of the second fluid cushion unit 34), so that air may penetrate into the fluid cushion 39 of the first fluid cushion unit 33 and/or into the fluid cushion 40 the second fluid cushion unit 34. As a result of a spring constant of the foam material, the foam material may expand within the shell, in that pockets of air arise between individual subareas of the foam material (e.g., air bubbles). In addition to the expansion properties in here and in the foam material, the gaseous filler (e.g., air) may be pumped into the fluid cushion 39 the first fluid cushion unit 33 and/or the fluid cushion 40 of the second fluid cushion unit 34 by the pump unit 43.

In a further embodiment, the first fluid cushion unit 33 may also have two or more fluid cushions 39. The second fluid cushion unit 34 may also have two or more fluid cushions 40. The individual fluid cushions 39, 40 of the first fluid cushion unit 33 and/or the second fluid cushion unit 34 may be filled exclusively with the gaseous filler or also with a foam material. The gaseous filler may be accepted at least partly into spaces and/or bubbles between individual foam elements and/or foam areas.

Although the invention has been illustrated and described in greater detail by the exemplary embodiments, the invention is not restricted by the disclosed examples. Other variations may be derived by the person skilled in the art, without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A hearing protection device comprising:
a first hearing protection unit for disposal on a first ear of a patient, the first hearing protection unit comprising a first fluid cushion unit having a first fluid cushion and a first opening;
a second hearing protection unit for disposal on a second ear of the patient, the second hearing protection unit comprising a second fluid cushion unit having a second fluid cushion and a second opening; and
a pump unit operable to feed a fluid into the first fluid cushion unit via the first opening, the second fluid cushion unit via the second opening, or a combination thereof,
wherein the first opening and the second opening are each individually configured to receive the fluid from the pump unit and to drain out the fluid.

2. The hearing protection device of claim 1, wherein the first hearing protection unit further comprises a first ear pad with a first ear accommodating area such that the first fluid cushion unit of the first hearing protection unit is disposed on a side of the first ear pad facing away from the first ear accommodating area, and
wherein the second hearing protection unit further comprises a second ear pad with a second ear accommodating area such that the second fluid cushion unit of the second hearing protection unit is disposed on a side of the second ear pad facing away from the second ear accommodating area.

3. The hearing protection device of claim 1, wherein the first fluid cushion and the second fluid cushion are each individually fillable with a filler.

4. The hearing protection device of claim 1, wherein the first fluid cushion and the second fluid cushion each individually comprise a foam material that is compressable in a first operating state and expandable in a second operating state as a result of a spring force of the foam material, and wherein each cushion accepts a filler.

5. The hearing protection device of claim 3, wherein the filler comprises air.

6. The hearing protection device of claim 1, wherein the first hearing protection unit and the second hearing protection unit each individually further comprise a shell having a flexible material that varies a shape and volume of the respective hearing protection unit.

7. The hearing protection device of claim 1, wherein the pump unit comprises a mechanical pump unit.

8. The hearing protection device of claim 1, wherein the first fluid cushion, the second fluid cushion, or both the first fluid cushion and the second fluid cushion comprise at least one valve unit.

9. A magnetic resonance device comprising:
a hearing protection device comprising:
a first hearing protection unit for disposal on a first ear of a patient, the first hearing protection unit comprising a first fluid cushion unit having a first fluid cushion and a first opening;
a second hearing protection unit for disposal on a second ear of the patient, the second hearing protection unit comprising a second fluid cushion unit having a second fluid cushion and a second opening; and
a pump unit operable to feed a fluid into the first fluid cushion unit via the first opening, the second fluid cushion unit via the second opening, or a combination thereof,
wherein the first opening and the second opening are each individually configured to receive the fluid from the pump unit and to drain out the fluid.

10. The magnetic resonance device of claim 9, wherein the first hearing protection unit further comprises a first ear pad with a first ear accommodating area such that the first fluid cushion unit of the first hearing protection unit is disposed on a side of the first ear pad facing away from the first ear accommodating area, and
wherein the second hearing protection unit further comprises a second ear pad with a second ear accommodating area such that the second fluid cushion unit of the second hearing protection unit is disposed on a side of the second ear pad facing away from the second ear accommodating area.

11. The magnetic resonance device of claim 9, wherein the first fluid cushion and the second fluid cushion are each individually fillable with a filler.

12. The magnetic resonance device of claim 9, wherein the first fluid cushion and the second fluid cushion each individually comprise a foam material that is compressable in a first operating state and expandable in a second operating state as a result of a spring force of the foam material, and wherein each cushion accepts a filler.

13. The magnetic resonance device of claim 11, wherein the filler comprises air.

14. The magnetic resonance device of claim 9, wherein the first hearing protection unit and the second hearing protection unit each individually further comprise a shell comprising a flexible material that varies a shape and volume of the respective hearing protection unit.

15. The magnetic resonance device of claim 9, wherein the pump unit comprises a mechanical pump unit.

16. The magnetic resonance device of claim 9, wherein the first fluid cushion, the second fluid cushion, or both the first fluid cushion and the second fluid cushion comprise at least one valve unit.

* * * * *